United States Patent [19]

Gale et al.

[11] Patent Number: 4,615,699
[45] Date of Patent: Oct. 7, 1986

[54] TRANSDERMAL DELIVERY SYSTEM FOR DELIVERING NITROGLYCERIN AT HIGH TRANSDERMAL FLUXES

[75] Inventors: Robert M. Gale, Los Altos; Randall G. Berggren, Livermore, both of Calif.

[73] Assignee: ALZA Corporation, Palo Alto, Calif.

[21] Appl. No.: 730,714

[22] Filed: May 3, 1985

[51] Int. Cl.$^4$ ............................................. A61K 9/00
[52] U.S. Cl. ..................................... 604/897; 424/28; 514/509; 514/964
[58] Field of Search ............... 604/897, 896, 890, 892; 424/28, 349

[56] References Cited

U.S. PATENT DOCUMENTS 4,201,211 5/1980 Chandrasekaran et al. ........ 604/897
4,294,820 10/1981 Keith et al. .......................... 604/897
4,346,709 8/1982 Schmitt ................................ 604/897
4,568,343 2/1986 Leeper et al. ....................... 604/897

Primary Examiner—John D. Yasko
Attorney, Agent, or Firm—Steven F. Stone; Paul L. Sabatine; Edward L. Mandell

[57] ABSTRACT

A high flux transdermal nitroglycerin therapeutic system is disclosed which is capable of delivering nitroglycerin through intact human skin at rates of 40 $\mu$g/cm$^2$hr and preferably in the range of 50–150 $\mu$g/cm$^2$hr. Ethanol delivered at a rate of from 250–500 $\mu$g/cm$^2$hr is employed as a permeation enhancer for the nitroglycerin and a rate controlling membrane formed from ethylene vinyl acetate having a vinyl acetate content greater than 11% and preferably between 12–18% provides the appropriate rate control for both the drug and the permeation enhancer. This system is suitable for use in treatment of angina pectoris and congestive heart failure.

19 Claims, 4 Drawing Figures

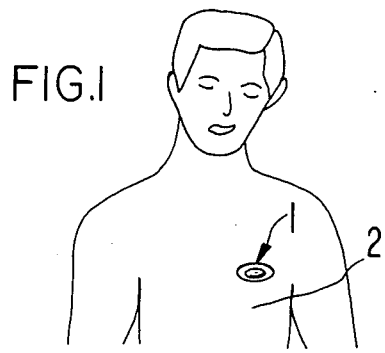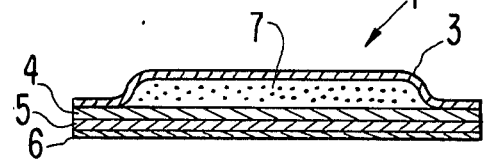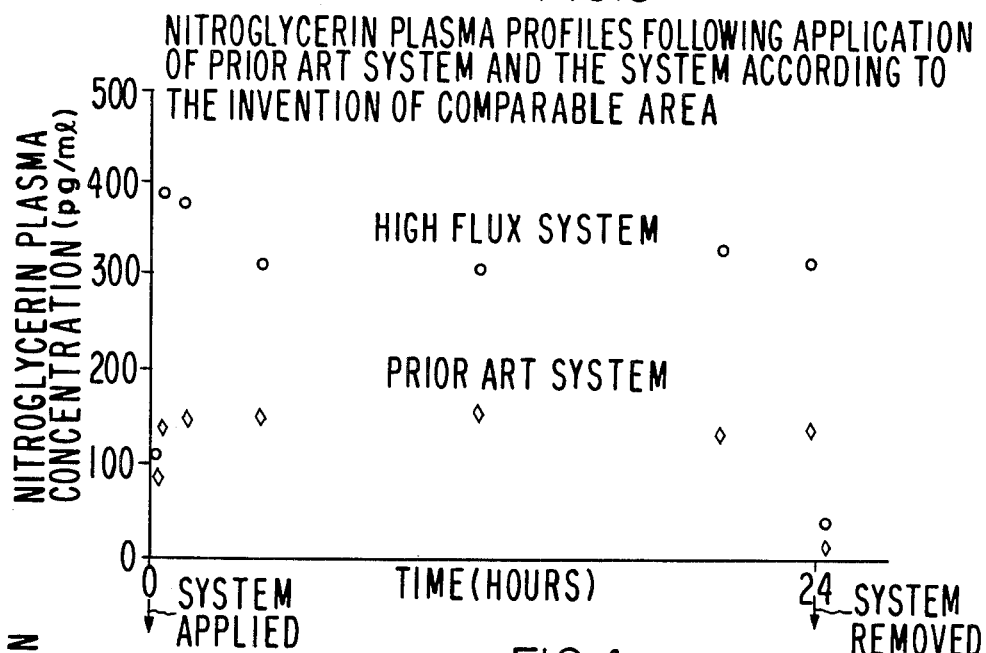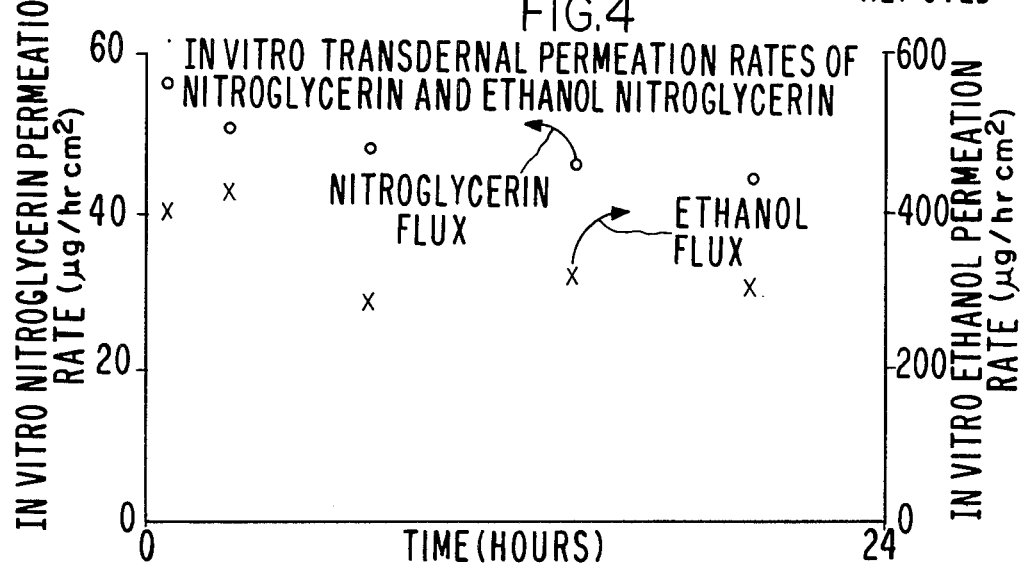

TRANSDERMAL DELIVERY SYSTEM FOR DELIVERING NITROGLYCERIN AT HIGH TRANSDERMAL FLUXES

FIELD OF THE INVENTION

This invention relates to a transdermal delivery device for the controlled transdermal delivery of nitroglycerin at in vivo transdermal fluxes of at least 40 $\mu g/cm^2/hr$ and preferably substantially higher, for use in the treatment of such conditions as angina pectoris and congestive heart failure.

BACKGROUND OF THE INVENTION

Nitroglycerin (NG) has long been recognized as a vasodilator having utility in the treatment of, among other indications, angina pectoris and congestive heart failure. NG was originally administered either orally or buccally and more recently transdermally. Transdermal NG drug delivery can be effected either through application of a gel or ointment such as the Nitrobid ® ointment to the skin or through the use of various commercially available transdermal NG delivery systems. A reasonably complete survey of the transdermal nitroglycerin products approved in the United States appears in an article entitled "Transdermal Drug Delivery", Curtis D. Black, Ph.D., *U.S. Pharmacist*, pages 49–78, November 1982. As indicated therein the approved transdermal NG delivery systems deliver NG at an average in vivo drug delivery rate of approximately 0.5 to 0.625 $mg/cm^2/24$ hrs, equivalent to approximately 20 to 26 $\mu g/cm^2 hr$. Another system, the Deponit system which has been approved in Europe, delivers NG at a rate of approximately 15 $\mu g/cm^2 hr$. Patents relating to such delivery systems include U.S. Pat. Nos. 4,191,015 and 3,742,951 and co-pending co-assigned patent application Ser. No. 278,364 filed June 29, 1981 for a Bandage for Administering Beneficial Drug, the corresponding South African Patent having been issued as African Pat. No. 82/0124, dated 29 December 1982, all of the above U.S. Patent being incorporated herein by reference.

Although the approved products have received wide patient acceptance, the total daily NG dose obtained from these systems is not adequate to provide the substantial NG doses required in the treatment of congestive heart failure or recalcitrant cases of angina pectoris. In order to obtain the needed daily doses of greater than 40 mg, a multiplicity of the existing systems would have to be applied or systems of substantially increased surface areas developed, neither of which is considered acceptable by the patients. Although it has been suggested in U.S. Pat. Nos. 4,191,015 and 3,742,951 to increase transdermal NG delivery rates by the co-administration of a permeation enhancer and NG and U.S. Pat. No. 4,262,003 which is incorporated herein by reference discloses the controlled delivery of a permeation enhancer as a means of controlling the rate of drug delivery, we are unaware of any transdermal NG delivery system specifically designed to deliver NG transdermally at controlled in vivo fluxes greater than 40 $\mu g/cm^2 hr$ and preferably in the range of 50 to 150 $\mu g/cm^2 hr$.

It is accordingly an object of this invention to provide a transdermal drug delivery system which is capable of delivering NG through intact skin at a controlled in vivo transdermal delivery rate of at least 40 $\mu g/cm^2 hr$ for extended periods of time of at least about 16 hours and preferably 24 hours or even multiples thereof.

It is another object of this invention to provide a transdermal NG drug delivery system suitable for use in the treatment of angina pectoris.

It is another object of this invention is to provide a transdermal nitroglycerin drug delivery system suitable for use in congestive heart failure.

It is another object of this invention to provide a transdermal nitroglycerin delivery system for the co-administration of nitroglycerin and a skin permeation enhancer for nitroglycerin.

These and other objects of the invention will be apparent from the following description with reference to the accompanying drawings wherein:

FIG. 1 is a plan view of a controlled transdermal NG delivery system according to this invention being worn by a patient;

FIG. 2 is a schematic cross-sectional representation of a controlled transdermal NG delivery system according to this invention;

FIG. 3 is a plot showing average NG plasma levels as a function of time for a representative NG delivery device of the prior art and a high flux NG delivery device according to this invention; and FIG. 4 is a plot showing in vitro NG and ethanol fluxes through cadaver skin into an infinite sink at 32° C. of an embodiment of their invention.

DESCRIPTION OF THE INVENTION

In order to achieve the daily NG dose required according to this invention at in vivo NG fluxes which are controlled primarily by the properties of the delivery system; it is necessary that the NG delivery system possess certain specific characteristics as hereinafter defined.

As used herein, the steady state drug flux through skin is considered to be substantially constant if it varies no more than about ±20% during the steady state delivery period. The steady state delivery period is defined as that portion of the total delivery period occurring (a) after the initial transient period characterized by an initially high delivery rate to the skin and (b) up to the reduction of the NG concentration in the drug reservoir to the point that the thermodynamic activity of the reservoir drops below 1 or the system is removed, whichever occurs first.

The steady state, in vivo drug input rate, Jnet, of agent, such as a drug or permeation enhancer delivered through the skin from a transdermal therapeutic system is given by the following relationship:

$$\frac{1}{J_{net}} = \frac{1}{J_{skin}} + \frac{1}{J_{system}} \quad (1)$$

wherein Jsystem is the in vitro steady state flux of agent from the system directly into an infinite sink and Jskin is the in vivo or in vitro steady state inherent flux of agent directly through skin from a unit activity source into an infinite sink, all units being expressed in $\mu g/cm^2 hr$.

As used herein a transdermal delivery device is considered to be system controlled when:

$$\frac{J_{net}}{J_{system}} \times 100 \geqq 50\% \quad (2)$$

Because Jskin, the inherent permeability of normal human skin to NG, is in the range of about 10–50

μg/cm²hr with average skin being about 40 μg/cm²hr, it is clear that it is impossible to achieve the in vivo drug fluxes contemplated herein from a system controlled delivery device unless the effective permeability of the skin to nitroglycerin is substantially increased throughout the delivery period.

In order to obtain a system controlled transdermal NG delivery system, a NG permeation enhancer must be delivered to the skin at rates sufficient to increase the NG permeability of even the most impermeable skin to a value at least equal to Jsystem and preferable to at least 2.4 times the steady state Jsystem to produce a device which is about 70% system controlled.

Referring now to FIGS. 1 and 2, a transdermal therapeutic system 1 according to this invention is shown in FIG. 1 placed on the intact skin of a patient. The system 1 is preferably fabricated in the form of a laminated pouch formed from an impermeable backing 3 bonded at its periphery to, and spaced apart at its central portion from, a NG release rate controlling membrane 4 which is coated with a contact adhesive 5 provided with a protective removable liner 6 intended to be stripped from the device prior to use. Although the preferred embodiment illustrated herein shows the use of an in-line adhesive 5 other means for holding the system in NG and permeation enhancer transmitting relationship to the skin include circumferentially located adhesives, adhesive overlays, belts, buckles, elastic bands or the like. The pouch is filled with a composition 7 which comprises the NG and permeation enhancer reservoir preferably in the form of a viscous gel or paste. Certain critical interrelationships between the compositions of the membrane 4 and the drug-enhancer reservoir 7 of the transdermal NG delivery system must exist according to this invention.

According to this invention we have found that ethanol can increase the Jskin for NG to levels sufficient to permit the NG Jnet to be in the required range of from 40-150 μg/cm²hr if the Jnet of ethanol delivered through the skin is at least about 250 μg/cm²hr and preferably higher but no greater than about 500 μg/cm²hr, the level at which unacceptable skin reactions are observed after one day applications. We have found that the permeability of average human skin to 95% ethanol is in the range of about 1200 to 1500 μg/cm²hr and therefore the ethanol Jsystem of the delivery device according to this invention should be in the range of about 300 to 750 μg/cm²hr to obtain the above target ethanol Jnet of 250-500 μg/cm²hr with 50% system control. We have also found that ethylene vinyl acetate (EVA) membranes having a vinyl acetate (VA) content of at least 11% and preferably in the range of 12-18% possess the necessary characteristics to maintain the flux of both the NG and ethanol within the ranges required according to this invention.

In addition, it is necessary that certain minimum drug and ethanol loadings be present in the reservoir such that the delivery device will function to deliver the nitroglycerin and ethanol throughout the selected administration period, preferably at least about 16 hours. A 16 hour system permits application in the morning upon awakening and provides for interruption during normal sleeping hours either by removal prior to bedtime or by depletion of the system. This regimen is appropriate for subjects who develop a NG tolerance on continuous use. The 24 hour or multiple thereof system provides for continuous therapy. In both cases however application of the transdermal delivery device at a certain particular time facilitates compliance.

The minimum NG loading per cm² of the system is determined by the solubility of the NG in the reservoir 7 and the in vivo delivery rate, sufficient NG being required to maintain the thermodynamic activity of the reservoir at unity (saturated solution) substantially throughout the delivery period. Because the maximum NG delivery rate is controlled by the release rate controlling membrane 4, the ethanol can be, but need not be, delivered at a substantially constant rate. Instead, whether delivered at a constant or decreasing rate during the NG delivery period, the ethanol Jsystem must be sufficient to maintain the NG Jskin in the desired range; i.e., the ethanol Jsystem should be in the range of from about 300-750 μg/cm²/hr. This ethanol flux can be obtained if sufficient ethanol is present to maintain the activity of ethanol at a level no lower than about 0.2 during the NG administration period.

The reservoir composition according to this invention comprises a carrier, preferably gelled, having a low solubility, below about 5 mg/gm, for NG and ethanol, and having the NG and the ethanol dispersed therethrough. We have found it difficult, if not impossible, to form a stable dispersion of ethanol in the typical NG-hydrophobic carrier matrix, such as silicone fluid and polyisobutylene-mineral oil gels, for example, because ethanol is insoluble in such carriers and tends to separate into small pools on standing. Further these pools can contain substantial amounts of dissolved nitroglycerin extracted from the lactose NG carrier due to the high solubility of NG in ethanol. We have found that it is necessary to absorb physically the ethanol on a porous carrier such as colloidal silica or porous polypropylene such as Accurel ® polypropylene or any other chemically compatible particulate carrier which is capable of absorbing a substantial amount of ethanol while retaining the appearance of a dry powder. The ethanol loaded powder can then be physically admixed with the carrier and the separation of ethanol prevented. The nitroglycerin and ethanol loaded carriers are then pouched within the device at loadings of at least about 1 and 5 mg/cm² of releasing surface respectively to obtain at system having a minimum useful life of about 16 hours.

The aforementioned patents and applications and U.S. Pat. No. 4,144,317, which is incorporated herein by reference, disclose various materials that can be used to form the backing member, carrier, gelling agent, rate controlling membrane and adhesive. A preferred embodiment of this invention employs silicone medical fluid as the carrier, colloidal silica as the gelling agent, colloidal silica or Accurel ® as the ethanol absorbent and an ethylene/vinyl acetate copolymer (EVA) membrane having a minimum of 11% VA and preferably 12-18% VA as the rate controlling membrane at a typical thickness of about 0.001-0.003 inches. The higher the VA content of the EVA, the greater the permeability to both NG and ethanol and within this range the NG and ethanol fluxes can be maintained within the desired ranges. The ethanol may be included a absolute alcohol although it is preferred, particularly from a cost standpoint to utilize the aqueous USP 95% ethanol. More dilute ethanol solutions can be employed provided the ethanol activity is maintained above about 0.2 throughout the useful life of the system. The lower the initial activity, the lower the initial ethanol release rate from the system will be. Thus, more dilute ethanol solutions could be of value if the initial transient ethanol flux through the skin would otherwise be significantly above about 500 µg/cm²hr during the initial, transient, high ethanol release rate phase. Having thus generally described our invention the following specific examples are provided.

EXAMPLE 1

A NG/ethanol reservoir composition comprising a silicone medical fluid carrier gelled with silica, having NG on lactose uniformly dispersed therethrough and ethanol absorbed in a particulate carrier is fabricated by placing 5 kg of silicone medical fluid having a viscosity of about 100 centistokes and 175 grams of colloidal silicon dioxide in a high energy mixing vessel and blending to produce a gelled silicone fluid. 200 Grams of Accurel ® porous polypropylene available from ARMAK Company is placed in a separate vessel and approximately 600 grams of USP ethanol (95% ethanol) is added with stirring to produce an essentially dry flowable powder which on visual observation appears to have absorbed substantially all of the ethanol. 5 kg of nitroglycerin-lactose (10 wt % nitroglycerin) and the ethanol loaded porous polypropylene is placed in the original high energy mixing vessel and mixed until a homogeneous blend is obtained. A form-fill-seal pouching machine is used to pouch the NG-ethanol gel so formed between an impermeable backing member comprising a medium density polyethylene/aluminized polyester/ethylene vinyl acetate multilaminate (Medpar ® 1006 available from Minnesota Mining & Manufacturing Company) peripherally thermosealed to the rate controlling membrane layer of a trilaminate film consisting of a release liner layer formed from polyester film coated with a film release agent, an adhesive layer formed of silicone medical adhesive and a release rate controlling membrane layer formed from a 1 mil thick EVA (12% VA) membrane to produce NG and ethanol loadings of 2.6 mg/cm² and 4.8 mg/cm² of ethanol respectively. Systems can be fabricated having NG/ethanol releasing surface areas of varying sizes such as approximately 5 cm², 10 cm² and 20 cm² for example. The in vivo plasma concentrations to be obtained upon the application of a 5 cm² system to a normal human subject is shown in FIG. 3. The in vitro release rates through cadaver skin of nitroglycerin and ethanol to be obtained from such a system into an infinite sink at 32° C. is shown in FIG. 4.

EXAMPLE 2

A transdermal therapeutic system is fabricated according to procedure of Example 1 except that the ethanol is adsorbed on 200 grams of silicon dioxide. The release rates will be substantially the same as for that of Example 1.

EXAMPLE 3

A system similar to that of Example 1 was fabricated using EVA (18% VA) film instead of the EVA (12% VA) film and with loadings of 5 mg nitroglycerin per cm² and 20 mg of 70% ethanol per cm². The systems will release nitroglycerin at a pattern similar to that found in FIGS. 2 and 3, except that they will be approximately 80% higher.

Having thus, this generally described our invention and preferred specific embodiments thereof it is apparent that various modifications and substitutions can be made by workers skilled in the art without departing from the scope of this invention which is limited only by the following claims wherein:

We claim:

1. A medical device for the high-flux, transdermal delivery of nitroglycerin over an extended time period comprising, in combination:
   (a) an impermeable backing member;
   (b) a NG release rate controlling membrane;
   (c) a nitroglycerin-ethanol reservoir maintained therebetween, said reservoir composition comprising a carrier having nitroglycerin and ethanol uniformly dispersed therethrough; and
   (d) means for maintaining said system in nitroglycerin and ethanol transmitting relationship to the skin;
   said device being characterized by a Jnet for nitroglycerin of at least 40 µg/cm²hr and a Jnet of ethanol in the range of about 250–500 µg/cm²hr.

2. The medical device according to claim 1 wherein said reservoir contains nitroglycerin and ethanol in amounts sufficient to deliver nitroglycerin and ethanol for at least about 16 hours.

3. The medical device of claim 2 wherein the nitroglycerin Jnet is in the range of about 50–150 µg/cm²hr.

4. The medical device of claim 1 wherein undissolved ethanol in said nitroglycerin-ethanol reservoir is adsorbed within a particulate carrier.

5. The medical device of claim 1 wherein said release rate controlling membrane is an ethylene vinyl acetate copolymer.

6. The medical device of claim 5 wherein the vinyl acetate content of said ethylene vinyl acetate copolymer is in the range of about 11–18%.

7. The medical device of claim 2 wherein said nitroglycerin steady state Jnet is substantially constant for a substantial portion of said time period and the ethanol steady state Jnet decreases within the range of 250–500 µg/cm²hr over a substantial portion of said time period.

8. The medical device of claim 2 wherein the steady state Jnet of the nitroglycerin and the ethanol remains substantially constant throughout a substantial portion of said time period.

9. A composition of matter suitable for use in the high flux transdermal delivery of nitroglycerin comprising in combination, a carrier containing nitroglycerin and ethanol uniformly dispersed therethrough and said carrier having a solubility for nitroglycerin and ethanol of less than about 5 mg/gram, said ethanol being present in amounts greater than 50 µg/gm with substantially all of the undissolved ethanol being distributed uniformly through the carrier within the pores of a porous particulate adsorbent.

10. The composition of claim 9 wherein said porous adsorbent is selected from a group consisting of silica and porous polypropylene.

11. A medical device for the high flux transdermal delivery of nitroglycerin through a predetermined area of skin comprising, in combination:
   (a) an impermeable backing;
   (b) a release rate controlling membrane;
   (c) a nitroglycerin permeation enhancer reservoir disposed between said backing and said membrane, said reservoir comprising a carrier having nitroglycerin and a skin permeation enhancer therefor dispersed through said carrier at concentrations above their saturation concentration in said carrier; substantially all of said undissolved permeation enhancer being contained within the pores of a porous particulate adsorbent; and (d) means of maintaining said device in nitroglycerin and permeation enhancer transmitting relationship to the skin.

12. The medical device of claim 11 wherein said permeation enhancer is ethanol and said rate controlling membrane is an ethylene/vinyl acetate copolymer.

13. The medical device of claim 12 wherein the vinyl acetate content of said copolymer is in the range of about 11–18%.

14. The medical device of claim 13 wherein said nitroglycerin and ethanol are present in amounts of at least 1 mg/cm$^2$ and 5 mg/cm$^2$, respectively.

15. The medical device of claim 11 wherein said means for maintaining the device on the skin is a nitroglycerin and permeation enhancer permeable adhesive disposed between said membrane and the skin.

16. The medical device of claim 6 wherein said means for maintaining the device on the skin is a nitroglycerin and ethanol permeable adhesive disposed between said membrane and the skin.

17. The medical device of claim 1 wherein said carrier is a silicone fluid.

18. The composition of claim 9 wherein said carrier is a silicone fluid.

19. The medical device of claim 10 wherein said carrier is a silicone fluid.

* * * * *